US00PP29019P2

(12) United States Plant Patent
Danziger

(10) Patent No.: US PP29,019 P2
(45) Date of Patent: Feb. 27, 2018

(54) ***PETUNIA* PLANT NAMED 'DAMORMIO'**

(50) Latin Name: *Petunia hybrida*
Varietal Denomination: DAMORMIO

(71) Applicant: Gavriel Danziger, Beit Dagan (IL)

(72) Inventor: Gavriel Danziger, Beit Dagan (IL)

(73) Assignee: Danziger "DAN" Flower Farm (IL)

( * ) Notice: Subject to any disclaimer, the term of this patent is extended or adjusted under 35 U.S.C. 154(b) by 0 days.

(21) Appl. No.: 15/330,925

(22) Filed: Nov. 14, 2016

(51) Int. Cl.
*A01H 5/02* (2006.01)

(52) U.S. Cl.
USPC ..... Plt./356.13

(58) Field of Classification Search
USPC ..... Plt./263.1, 356.1, 356.13
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Petunia* cultivar named 'DAMORMIO' is disclosed, characterized by very well branched, mounded plants with a medium vigor. Flower color pink with white stripes, forming unique heart shaped patterns along the margins under high light conditions. Flower size is large and plants flower abundantly. The new variety is a *Petunia*, suitable as an outdoor garden or container plant.

3 Drawing Sheets

Latin name of the genus and species: *Petunia hybrida.*

Variety denomination: 'DAMORMIO'.

The new *Petunia* cultivar resulted as part of a planned breeding program by the inventor Gavriel Danziger. The objective of the breeding program was to develop new *Petunia* varieties with interesting color patterns and attractive plant forms.

The new variety resulted from the crossing of the seed parent, an unpatented, proprietary seedling referred to as 'c.v. 12-6708', with the pollen parent is an unpatented, proprietary seedling referred to as 'c.v. 13-6934' in October of 2013. The new variety was discovered in July 2014 by the inventor in a group of seedlings resulting from the October of 2013 crossing in a research greenhouse in Moshav Mishmar Hashiva, Israel.

Asexual reproduction of the new cultivar 'DAMORMIO' by vegetative cuttings was first performed at a greenhouse as well as outdoors in Moshav Mishmar Hashiva, Israel in July of 2014. Subsequent propagation by vegetative cuttings has shown that the unique features of this cultivar are stable and reproduced true to type in several successive generations.

SUMMARY OF THE INVENTION

The cultivar 'DAMORMIO' has not observed under all possible environmental conditions. The phenotype may vary somewhat with variations in environment such as temperature, day length and light intensity, without however, any variance in genotype.

The following traits have been repeatedly observed and are determined to be the unique characteristics of 'DAMORMIO'. These characteristics in combination distinguish 'DAMORMIO' as a new and distinct *Petunia* cultivar:

1. Mounded growth habit.
2. Very well branched plants with medium vigor.
3. Flower color is pink with white stripes forming a unique pattern, which can resemble a heart shape along the margin under high light conditions.

4. Flower size is large
5. Abundant flowering

COMPARISON TO THE PARENT VARIETY

Plants of the new cultivar are similar to plants of the seed parent, most horticultural characteristics, however, plants of the new cultivar differ in the following;

1. Plants of the seed parent are semi-upright, plants of the new variety are mounding.
2. The seed parent variety is more compact and not very well-branched.
3. Seed parent flower color is white with red stripes.
4. Seed parent flower size is extra-large, the new variety has a large flower.
5. The new variety flowers more abundantly than the seed parent.

Plants of the new cultivar are similar to plants of the pollen parent, most horticultural characteristics, however, plants of the new cultivar differ in the following;

1. The pollen parent has a trailing growth habit, the new variety is mounded.
2. The pollen parent is not as well-branched as the new variety.
3. Flower size of the pollen parent is medium, flower size of the new variety is large.
5. The new variety flowers more abundantly than the pollen parent.

COMPARISON TO COMMERCIAL VARIETIES

Plants of the new cultivar can be compared to the patented commercial variety *Petunia* 'DRAY67' U.S. Plant Pat. No. 25,906. These varieties are similar in most horticultural characteristics; however, the new cultivar differs in the following:

1. Flower size of the comparator is smaller than the flower of the new variety

2. Comparator flower color is black with yellow stripes, while the new variety has pink flowers with white stripes.
3. Plants of the comparator are taller than plants of the new variety.

Plants of the new cultivar can be compared to the commercial variety *Petunia* 'Dancas305', unpatented. These varieties are similar in most horticultural characteristics; however, the new cultivar differs in the following:

1. Flower size of the comparator is smaller than the flower of the new variety
2. Flower color of the comparator is purple with white stripes, while the new variety has pink flowers with white stripes.
3. Plant habit of the comparator is semi-trailing, while the new variety has a mounded growth habit.

BRIEF DESCRIPTION OF THE PHOTOGRAPHS

The accompanying photograph in FIG. 1 illustrates in full color a typical plant of 'DAMORMIO' grown in a greenhouse, in a 20 cm pot. Age of the plant photographed is approximately 3 months old from 5 rooted cuttings. Plants in FIG. 1 were grown under high light conditions, photographed during May.

Figure 1:
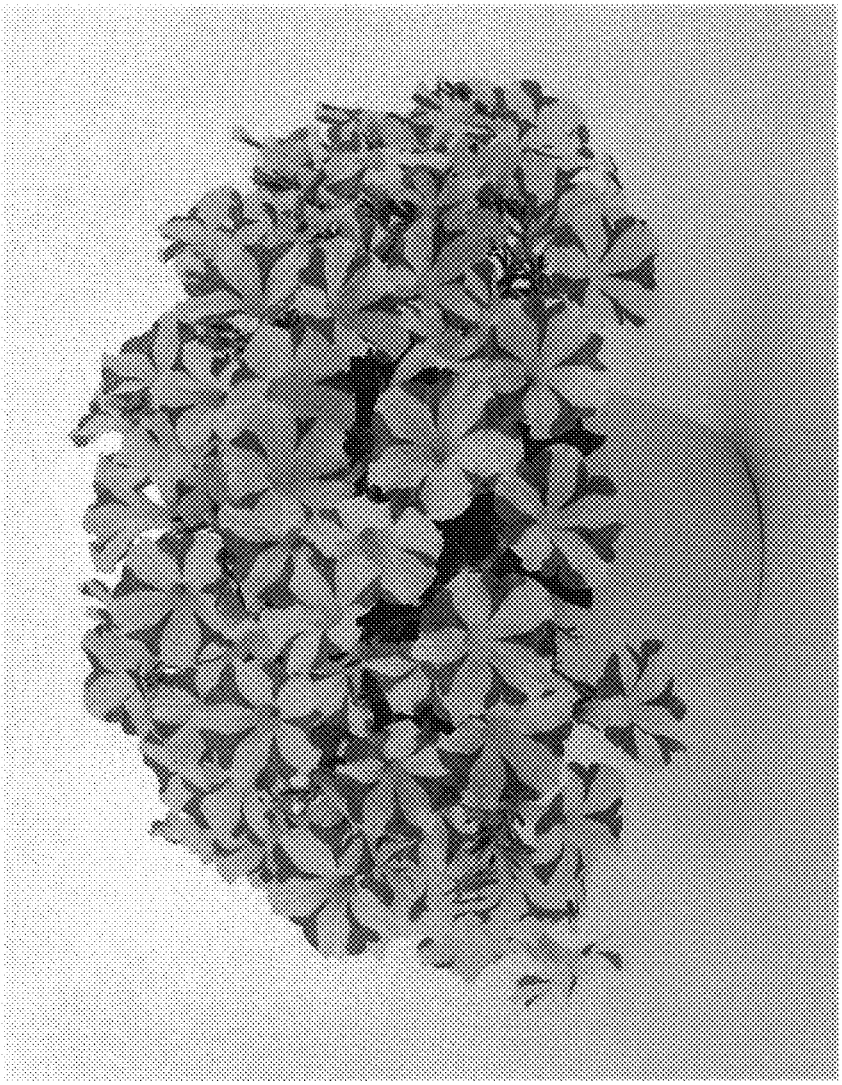
Figure 2:
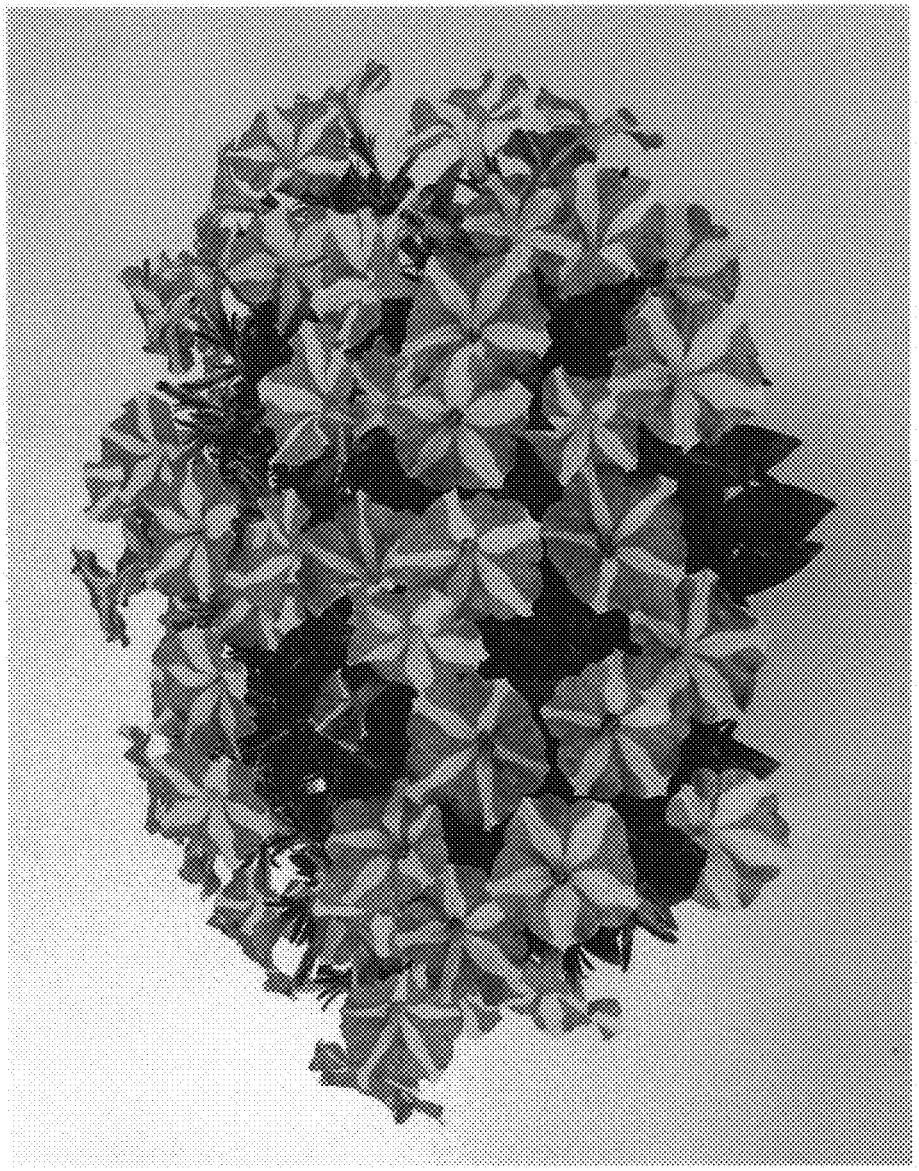
FIG. 2 illustrates similarly aged plants grown in the same pot size as plants in FIG. 1. Plants in FIG. 2, however were grown under lower light conditions and photographed in October.
Figure 3:
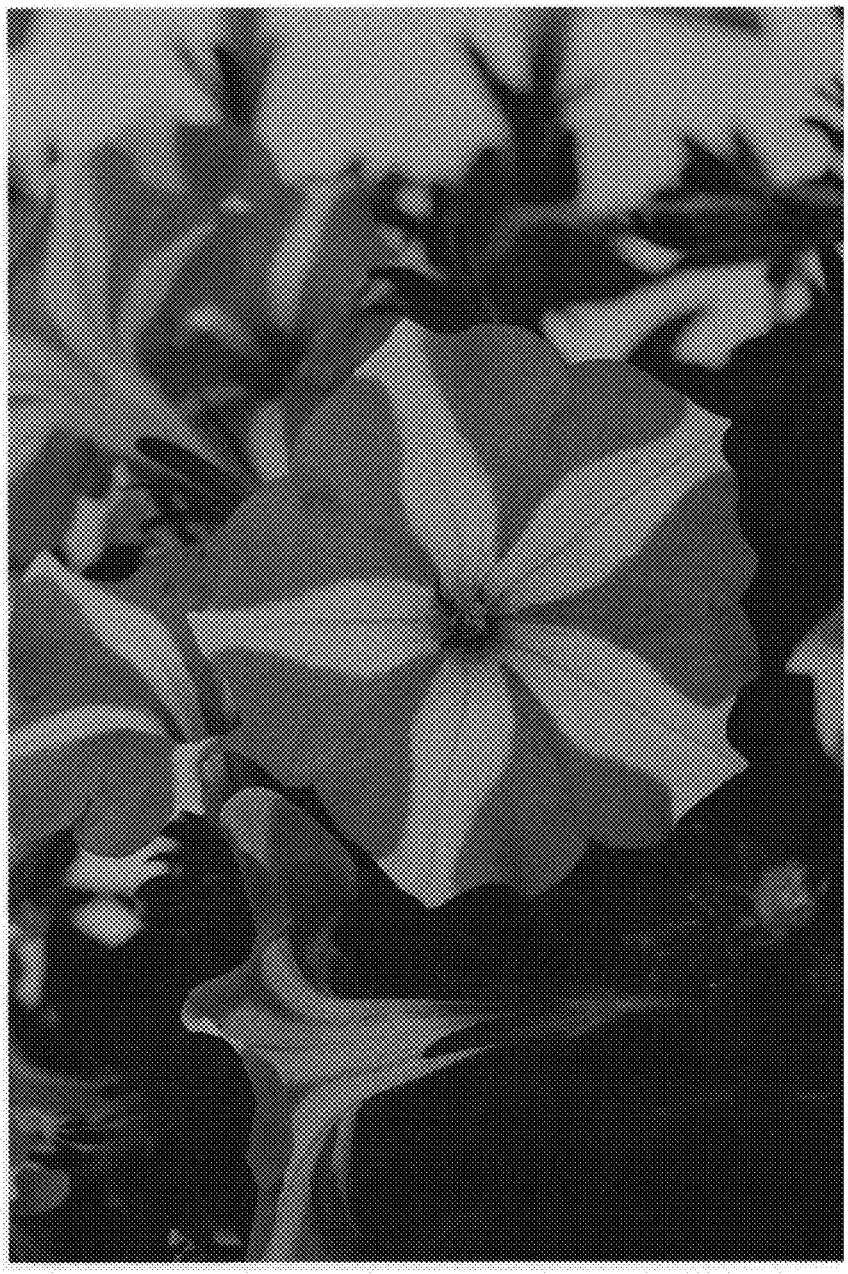
FIG. 3 illustrates a close up view of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005, except where general terms of ordinary dictionary significance are used. The following observations and measurement describe 'DAMORMIO' plants grown in a greenhouse and outdoors in Moshav Mishmar Harshiva, Israel during the spring, summer, and autumn. The growing temperature ranged from 20° C. to 35° C. day, 17° C. to 23° C. night. General light conditions are bright, normal sunlight with some shade during the brightest part of the day. Measurements and numerical values represent averages of typical plant types.

Botanical classification: *Petunia hybrida.*

PROPAGATION

Time to initiate roots: About 10 to 14 days at approximately 20° C.

Root description: Fibrous.

PLANT

Growth habit: Mounded.

Pot size of plant described: 13 cm.

Height: To top of flowers: about 20 cm.

Plant spread: About 45 cm.

Growth rate: Medium.

Branching characteristics: Very well branched.

Length of primary lateral branches: About 22 cm.

Diameter of lateral branches: About 0.3 cm.

Quantity of primary lateral branches: 8.

Characteristics of primary lateral branches:

*Form.*—Cylindrical.

*Diameter.*—About 0.3 cm.

*Color.*—RHS Yellow-Green 144B.

*Texture.*—Pubescent.

*Strength.*—Good.

Internode length: About 1.5 cm.

FOLIAGE

Leaf:

*Arrangement.*—Opposite.

*Quantity.*—Approximately 25 per branch.

*Average length.*—6.0 cm.

*Average width.*—2.5 cm.

*Shape of blade.*—Elliptic.

*Apex.*—Acute.

*Base.*—Acute.

*Margin.*—Entire.

*Texture of top surface.*—Velvety.

*Texture of bottom surface.*—Velvety.

*Aspect.*—90 degrees.

*Color.*—Young foliage upper side: RHS Green N 137 A. Young foliage under side: RHS Yellow-Green 146 A. Mature foliage upper side: RHS Green N 137 B. Mature foliage under side: RHS Yellow-Green 146 B.

*Venation.*—Type: Pinnate. Venation color upper side: RHS Yellow-Green 146 B. Venation color under side: RHS Yellow-Green 146 C.

*Petiole.*—Length: About 0.5 cm. Diameter: About 0.3 cm. Color: RHS Yellow-Green 146 B.

*Texture.*—Velvety.

FLOWER

Natural flowering season: Spring, Summer and Autumn under environmental conditions similar to Israel.

Days to flowering from rooted cutting: About 30 days.

Inflorescence and flower type and habit: Axillary, single flower, salverform shape, erect habit.

Rate of flower opening: 2 to 3 days from bud to fully opened flower.

Flower longevity on plant: 3-6 days.

Approximate quantity of flowers per plant: About 60.

Persistent or self-cleaning: Self-cleaning.

Bud:

*Shape.*—Tubular.

*Length.*—About 4.5 cm.

*Diameter.*—About 1 cm.

*Color.*—RHS Green-Yellow 1 C with 5 Stripes Red-Purple 60 C.

Flower size:

*Diameter.*—About 6 cm.

*Flower tube length.*—About 3 cm.

*Flower tube diameter at distal end.*—1.2 cm.

*Flower tube diameter at proximal end.*—0.3 cm.

Petals:

*Length from throat.*—About 2.5 cm.

*Width.*—About 2.8 cm.

*Quantity.*—5.

*Texture.*—Velvety.

*Apex.*—Acute.

*Margin.*—Wavy.

Color:

*When opening*.—Upper surface: Near RHS Red-Purple 60 B with 5 Stripes, White N155 C. Lower surface: RHS Red-Purple 60 C with 5 Stripes, White N155 C.

*Fully opened*.—Upper surface: RHS Red-Purple N57 B with 5 Stripes, White N155 C. Lower surface: Red-Purple N 57 C with 5 Stripes, White N155 C. Flower throat (inside): RHS Yellow 5 B with Veins, Red-Purple 60 A. Flower throat, vein: RHS Yellow-Green 151 C. Flower tube (outside): RHS Green-Yellow 1 C with 5 Stripes, Red-Purple 60 C. Flower tube, vein: RHS Yellow-Green 151 B.

*Fading*.—Petals fading to: RHS Red-Purple N 57 C with 5 Stripes, White NN 155 C.

Calyx/sepals:

*Quantity per flower*.—5.

*Shape*.—Linear.

*Length*.—About 2.5 cm.

*Width*.—About 0.4 cm.

*Apex*.—Acute.

*Base*.—Cuneate.

*Margin*.—Entire.

*Texture*.—Velvety.

*Color*.—Upper Surface: RHS Green 137 B. Lower Surface: RHS Green 137 C.

Pedicel:

*Length*.—About 2.5 cm.

*Diameter*.—About 0.2 cm.

*Color*.—RHS Yellow-Green 144 A.

*Orientation*.—45 degrees.

Fragrance: None.

REPRODUCTIVE ORGANS

Stamens:

*Number*.—5

*Filament length*.—About 2 cm. .

Anthers:

*Length*.—About 0.1 cm.

*Shape*.—Rounded.

*Color*.—RHS White N155 C.

*Pollen*.—Quantity: Abundant. Color: RHS White N155 B.

Pistil:

*Number*.—1.

*Length*.—About 2.5 cm.

*Style*.—Length: About 1.9 cm. Color: RHS Yellow-Green 144 D.

*Stigma*.—Shape: Rounded. Color: RHS Yellow-Green 144 C. Ovary Color: RHS Yellow-Green 144 B.

OTHER CHARACTERISTICS

Seeds and fruits:

Seeds and fruits: About 60 brown, rounded seeds of about 0.5 mm diameter, per one brown, conical capsule. Color not accurately measured with R.H.S. chart.

Disease/pest resistance: Neither resistance nor susceptibility to the normal diseases and pest of *Petunia* have been observed. Typical well known diseases include: *Botrytis cineria, Fusarium, Pythium, Phytophthora*, and *Rhizoctonia* species. Typical well known pests include: Leaf miners, spider mites, thrips and possibly caterpillars.

Temperature tolerance: Typical range from 5° to 40° C.

What is claimed is:

1. A new and distinct cultivar of *Petunia* plant named 'DAMORMIO' as herein illustrated and described.

* * * * *